US00PP15144P3

(12) United States Plant Patent
de Groot

(10) Patent No.: US PP15,144 P2
(45) Date of Patent: Sep. 14, 2004

(54) HYBRID TEA ROSE PLANT NAMED 'RUIMX19'

(50) Latin Name: *Rosa hybrida L.*
Varietal Denomination: Ruimx19

(75) Inventor: Henk C.A. de Groot, De Kwakel (NL)

(73) Assignee: De Ruiter's Nieuwe Rozen B.V., De Kwakal (NL)

( * ) Notice: Subject to any disclaimer, the term of this patent is extended or adjusted under 35 U.S.C. 154(b) by 0 days.

(21) Appl. No.: 10/437,869

(22) Filed: May 13, 2003

(65) Prior Publication Data

US 2003/0217397 P1 Nov. 20, 2003

(30) Foreign Application Priority Data

May 14, 2002 (EP) ..... 2002/0748

(51) Int. Cl.[7] ..... A01H 5/00

(52) U.S. Cl. ..... Plt./130

(58) Field of Search ..... Plt./130, 139, 138

*Primary Examiner*—Anne Marie Grunberg
*Assistant Examiner*—June Hwu

(74) *Attorney, Agent, or Firm*—Christie, Parker & Hale, LLP

(57) ABSTRACT

A new and distinct Hybrid Tea rose plant having attractive purple red flowers.

1 Drawing Sheet

Classification: The present invention relates to a new *Rosa hybrida L.* plant.

Varietal denomination: The new plant has the varietal denomination 'Ruimx19'.

BACKGROUND OF THE INVENTION

The present invention relates to a new and distinct variety of rose plant of the Hybrid Tea rose class, which was discovered as a natural branch mutation in a controlled planting of 'Ruidusty', unpatented.

SUMMARY OF THE INVENTION

Among the novel characteristics possessed by this new variety which distinguishes it from its parents and all other varieties of which I am aware are flowers of attractive purple red color.

Asexual reproduction by propagation by grafting of the new variety as performed in De Kwakel, The Netherlands shows that the foregoing and other distinguishing characteristics come true to form and are established and transmitted through succeeding propagation.

COMPARISON WITH PARENTS

Among other respects, the new variety differs from its parent in flower color, inasmuch as the parent has flowers ranging from orange red to yellow brown pink with cream yellow and purple red spots, whereas the new variety has flowers that are purple red.

BRIEF DESCRIPTION OF THE ILLUSTRATION

The accompanying illustration shows a typical specimen of the new variety depicted in color as nearly true as is reasonably possible to make the same in a color illustration of this character. In the illustration are shown new foliage 1; leaflets 2, 3 and 4; a stem with thorns 5; flowers in different stages of development 6, 7, 8 and 9; and reproductive organs 10, 11 and 12.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during January from a grafted cutting.

FLOWER

Blooming habit: Continuous.

Bud:
- *Size.*—Medium, about 37 mm length; 30 mm width.
- *Form.*—Ovate.
- *Color.*—Near 53A.

Sepals:
- *Size.*—Length about 40 mm, usually 3 sepals at the base about 13 mm width; convex to pointed, and 2 sepals with 2 to 5 foliated extensions, and a leaf-like extension at the top about 20 to 40 mm long, texture upper surface velvety, texture lower surface smooth.
- *Color.*—Near 144A.

Peduncle:
- *Length.*—Approximately 8 cm.
- *Aspect.*—Smooth.
- *Strength.*—Thin.
- *Color.*—Near 144A.

Bloom:
- *Size.*—About 8 cm.
- *Borne.*—Singly.
- *Form.*—Shape, side view, upper part is flat, lower part is concave.

Petalage: Approximately 25.

Color (⅓ to ½ open):

*Outer petals.*—Top Surface: Near 45B. Undersurface: Near 53D.
*Inner petals.*—Top Surface: Near 48A. Undersurface: Near 48C.
*Base of petals* (*point of attachment*).—Near 5A.
*General tonality from a distance.*—Purple red.

Color (fully opened):
*Outer petals.*—Top Surface: Near 63A. Undersurface: Near 61C.
*Inner petals.*—Top Surface: Near 51A. Undersurface: Near 48C.
*Base of petals* (*point of attachment*).—Near 5A.
*Color change.*—From purple red to purple pink. Petal Top Surface: Near 54A. Petal Undersurface: Near 54B.
*General tonality from a distance.*—Purple pink.

Petals:
*Texture.*—Smooth, thick.
*Appearance.*—Inside: Velvety. Outside: Velvety.
*Form.*—Round.
*Size.*—Petal length about 20 mm, width about 30 mm, petals reflex, outermost petals reflex backward at opening, fully open, all petals reflex backwards.
*Margin.*—Entire.
*Arrangement.*—Regularly arranged.
*Petaloids in center.*—Approximately 8, length about 10 to 13 mm, width about 9 to 12 mm, color upper surface near 51A, color lower surface near 48C.
*Persistence.*—Very persistent.
*Fragrance.*—No fragrance.
*Lasting quality.*—On the plant: Approximately 5 days. In the vase: Approximately 13 days.

REPRODUCTIVE ORGANS

Stamens, Filaments and Anthers:
*Arrangement.*—Regularly arranged around styles.
*Color.*—Stamens: Filaments: Near 5A. Anthers: Near 20A. Pollen: Near 161B. Stigmas: Near 4D.
*Hips.*—Hips and seeds have not been observed because the plant has never been grown to the stage of seed development and the variety is grown for producing flower stems.
*Size.*—Filaments: About 4 to 6 mm. Anthers: About 1 to 2 mm. Styles: Bunched, uneven length, longer than stamens, about 5 to 7 mm.

PLANT

Form: Narrow, bushy.
Growth: Uniform branching.
*Height attained* (*first season*).—Approximately 140 cm, average width about 50 to 60 cm.

Foliage:
*Top.*—Compound 3, 5 and 7 leaflet leaves.
*Size.*—Terminal leaflets length about 8 to 12 cm, width about 5 to 7 cm; other leaflets length about 6 to 7.5 cm, width 3.5 to 5 cm.
*Quantity.*—About 14 leaves per stem.
*Color.*—New foliage: Upper Side: Near 146A, edge color near 186B, surface not smooth. Underside: Near 186A. Mature foliage: Upper Side: Near 137A. Underside: Near 137C.
*Shape.*—Ovate.
*Texture.*—Upper Side: Unsmooth. Underside: Matte.
*Edge.*—Serrated.
*Serration.*—Serrate.
*Petiole.*—Texture smooth. Top Surface: Near 146D and near 184B. Underside: Near 146D.

Stipules: About 4 mm; top surface near 146D; underside near 146B, top surface smooth, under surface smooth.
Auricle: Not present.
Rachis: Average length about 9 cm; underside is smooth with about 1 to 2 prickles; near 146B.

Wood:
*New shoots.*—Color: Bark: Near 152A. Wood: Near 144A. Bark: Smooth.
*Old wood.*—Color: Bark: Near 138A. Wood: Near 150D.
*Bark.*—Smooth.
*Flower stem length* (*from last cut*).—Approximately 75 cm.

Thorns:
*Quantity.*—On lower portion of stem about 3 to 4 thorns between internodes; on top (⅓) no thorns; on laterals from basal canes, occasional.
*Length.*—About 7 mm.
*Color* (*when young*).—Near 174C.
*Color* (*when mature*).—Near 165C.
*Position.*—Irregular on the lower part of stem.
*Prickles.*—Some.

I claim:

1. A new and distinct Hybrid Tea rose plant of the variety substantially as shown and described.

* * * * *

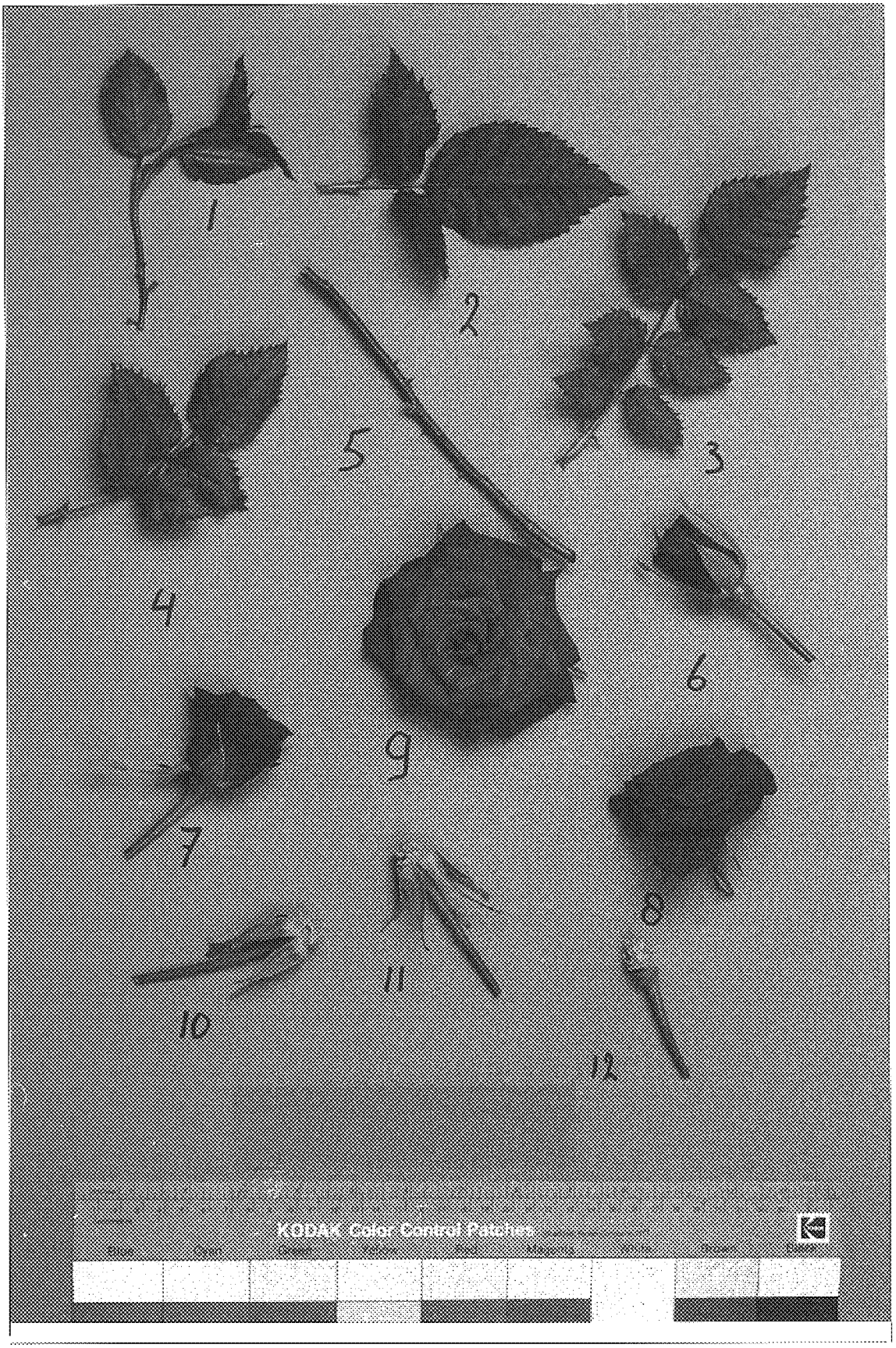
1
2
3
4
5
6
7
8
9
10
11
12
KODAK Color Control Patches